United States Patent [19]

Scholtysik

[11] 4,046,917

[45] Sept. 6, 1977

[54] METHOD OF TREATING MIGRAINE

[75] Inventor: Günter Scholtysik, Reinach, Switzerland

[73] Assignee: Sandoz Ltd., Basel, Switzerland

[21] Appl. No.: 678,241

[22] Filed: Apr. 19, 1976

[30] Foreign Application Priority Data

Apr. 23, 1975 Switzerland .......................... 5205/75

[51] Int. Cl.$^2$ ........................................... A61K 31/155
[52] U.S. Cl. ...................................................... 424/326
[58] Field of Search .......................................... 424/326

[56] References Cited

FOREIGN PATENT DOCUMENTS 1,793,483            Germany

OTHER PUBLICATIONS

Shipley et al., Proc. Soc. Exp. Biol., (1947) 64–453.

*Primary Examiner*—Stanley J. Friedman
*Attorney, Agent, or Firm*—Gerald D. Sharkin; Robert S. Honor; Walter F. Jewell

[57] ABSTRACT

The invention relates to a new use of 2,6-dichlorophenyl-acetylguanidine as an anti-migraine agent.

4 Claims, No Drawings

METHOD OF TREATING MIGRAINE

The invention relates to a new use of 2,6-dichlorophenyl-acetylguanidine (also known as N-Amidino-2,6-dichlorophenyl-acetamide).

2,6-dichlorophenyl-acetylguanidine has been described in the German D.O.S. No. 1,793,483. This compound has been clinically tested as an anti-hypertensive agent in patients suffering from hypertension using doses of, for example, 3–10 mg daily p.o.

It has now been found that 2,6-dichlorophenyl-acetylguanidine has an extremely favourable effect in the prophylaxis and treatment of migraine, as indicated by vasoconstrictor activity, hypertensive activity and a noradrenaline reinforcement effect in the pithed rat preparaion and by a tonicizing effect on isolated veins and arteries, for example as described in the following tests.

Brain and spinal cords of rats were pithed in accordance with the principles of R.E. Shipley and J.H. Tilden Proc. Soc. Exp. Biol. (1947) 64, 453. The pressor effect of 2,6-dichlorophenyl-acetylguanidine was subsequently measured in conventional manner.

The test showed that 2,6-dichlorophenyl-acetylguanidine has a hypertensive effect in the pithed rat preparation at doses of 10, 30 and 100 ug/kg i.v. The blood pressure increase appeared immediately after the injection and reached its maximum within 1 to 2 minutes. Phentolamine, an alpha-adrenoceptor-blocking substance at a dose of 2 mg/kg i.v. when injected 5 minutes before 2,6-dichlorophenyl-acetylguanidine inhibited practically completely the hypertensive effect. Pretreatment with 5 mg/kg i.p. of reserpine 24 hours prior to 2,6-dichlorophenyl-acetylguanidine at a dose of 100 ug/kg i.v. did not reveal any statistically significant influence on the hypertensive effect due to 2,6-dichlorophenyl-acetylguanidine.

The results of the tests in the pithed rat preparation show that 2,6-dichlorophenyl-acetylguanidine has a vasoconstrictor and thus hypertensive effect caused by direct stimulation of vascular alpha-adrenoceptors.

A further test in the pithed rat preparation showed that 2,6-dichlorophenyl-acetylguanidine reinforces, in a dose-dependent manner, the pressor effect of noradrenaline (sub-maximal dose from 0.5 μg/kg i.v.). An increase of the noradrenaline effect by 50% was achieved by a dose of 0.013 mg/kg i.v. of 2,6-dichlorophenyl-acetylguanidine.

Furthermore, 2,6-dichlorophenyl-acetylguanidine has a tonicizing effect in vitro on veins and arteries in accordance with the principles of E. Muller-Schweinitzer and E. Sturmer Br.J. Pharmac. (1974) 51, 441–446. This can be shown in spiral strips of the Aorta thoracalis from the rabbit and the Vena palmaris metacarpalis profunda from the cow. A concentration of from $10^{-8}$ to $10^7$ g/ml of the compound 2,6-dichlorophenyl-acetylguanidine shows a similar to that of noradrenaline. In general the contraction on the vein is stronger than that on the artery.

For the above use, the dose to be administered is dependent on the mode of administration and the treatment desired. Satisfactory results are obtained upon administration of 2,6-dichlorophenyl-acetylguanidine at a daily dose of between 0.03 and 10 mg/kg.

The daily dose of 2,6-dichlorophenyl-acetylguanidine for large mammals amouts to between 2 and 20 mg p.o. This amount may also be administered in divided doses two to four times daily or in sustained release form.

The compound may be administered in the form of tablets, powders, granules, capsules, etc. Aside from the compound the preparations may contain pharmaceutically inert organic or inorganic adjuvants, optionally granulating agents, lubricants, adhesives, etc. Adjuvants for the production of tablets may be microcrystalline cellulose, mannitol, lactose, etc. Granulating and disintegrating agents may be microcrystalline cellulose, etc. Binding agents may be polyvinylpyrolidone, methylcellulose and lubricants may be stearic acid, etc. Tablets may be coated or uncoated, with the coating being applied in manner know per se and having the purpose of delaying the disintegration and adsorption in the gastrointestinal tract, and thus providing a retarded effect over a long period. Capsules may contain the active substance either on its own or together with an inert solid diluent, for example, lactose, mannitol, and microcrystalline cellulose.

Solid preparations, especially hard-filled capsules and tablets, are preferred for reasons of easier production and favourable administration.

A preferred tablet preparation consists of 5 mg of 2,6-dichlorophenyl-acetylguanidine, 140 mg of lactose, 5 mg of polyvinyl-pyrolidone, 14 mg of microcrystalline cellulose, and 2 mg of stearic acid.

The compound is conveniently administered in pharmaceutically acceptable acid addition salt form. Such forms are known and include the hydrochloride.

A further example of a tablet formulation is as follows:

| | |
|---|---|
| 2,6-dichlorophenyl-acetylguanidine hydrochloride | 3.45 mg |
| lactose | 88.85 mg |
| microcrystalline cellulose | 12.0 mg |
| polyvinylpyrolidone | 3.7 mg |
| stearic acid | 2.0 mg |
| | 110.0 mg |

An example of a capsule formulation is as follows:

| | |
|---|---|
| 2,6-dichlorophenyl-acetylguanidine hydrochloride | 3.45 mg |
| lactose | 98.85 mg |
| microcrystalline cellulose | 15.0 mg |
| stearic acid | 2.7 mg |
| | 120.0 mg |

I claim:

1. A method of treating or preventing migraine in animals which comprises administering a therapeutically effective amount of the compound 2,6-dichlorophenyl-acetylguanidine to an animal in need of such treatment.

2. A method of claim 1, wherein the compound is administered at a daily dosage of from 0.03 to 10 mg/kg animal body weight.

3. The method of claim 3, wherein the compound is administered at a daily dosage of from 2 to 20 mg.

4. The method of claim 1, wherein the compound is administered in unit dosage form containing 0.05 to 5 mg.

* * * * *